(12) United States Patent
Dunbar et al.

(10) Patent No.: US 8,237,601 B2
(45) Date of Patent: Aug. 7, 2012

(54) REMOTE CONTROL DEVICE

(75) Inventors: Lee Dunbar, Bothell, WA (US);
Michael Reisenbichler, Bothell, WA (US); Scott N. Lockhart, Redmond, WA (US)

(73) Assignee: SonoSite, Inc., Bothell, WA (US)

( * ) Notice: Subject to any disclaimer, the term of this patent is extended or adjusted under 35 U.S.C. 154(b) by 828 days.

(21) Appl. No.: 12/251,249

(22) Filed: Oct. 14, 2008

(65) Prior Publication Data
US 2010/0090877 A1   Apr. 15, 2010

(51) Int. Cl.
*G08C 19/22* (2006.01)
(52) U.S. Cl. .................................. 341/176; 341/173
(58) Field of Classification Search .................. 341/176, 341/173
See application file for complete search history.

(56) References Cited

U.S. PATENT DOCUMENTS

| | | | |
|---|---|---|---|
| 7,289,825 B2 * | 10/2007 | Fors et al. | 455/556.1 |
| 2003/0083577 A1 | 5/2003 | Greenberg | |
| 2005/0265267 A1 | 12/2005 | Hwang | |
| 2006/0142740 A1 * | 6/2006 | Sherman et al. | 606/1 |
| 2007/0066894 A1 | 3/2007 | Bartol et al. | |
| 2007/0199804 A1 | 8/2007 | Joseph et al. | |
| 2008/0252793 A1 * | 10/2008 | Choi et al. | 348/734 |

OTHER PUBLICATIONS

International Search Report and the Written Opinion issued for PCT/US2009/055105, dated Feb. 19, 2010, 8 pages.

* cited by examiner

*Primary Examiner* — Danny Nguyen
(74) *Attorney, Agent, or Firm* — Fenwick & West LLP

(57) ABSTRACT

The present invention is directed to a system and method which allows a device user who is within a sterile environment to interact remotely with a device physically located outside of the sterile zone. In one embodiment, the remote link is wireless and allows the operator to adjust critical controls without breaking the sterile environment. The remote device is designed to be sheathed in sterile sheaths and further designed, in one embodiment, to keep the remote control element from physically interacting with the patient and in some cases with the device operator. In one embodiment, the remote device operator interacts with the remote device verbally.

28 Claims, 4 Drawing Sheets

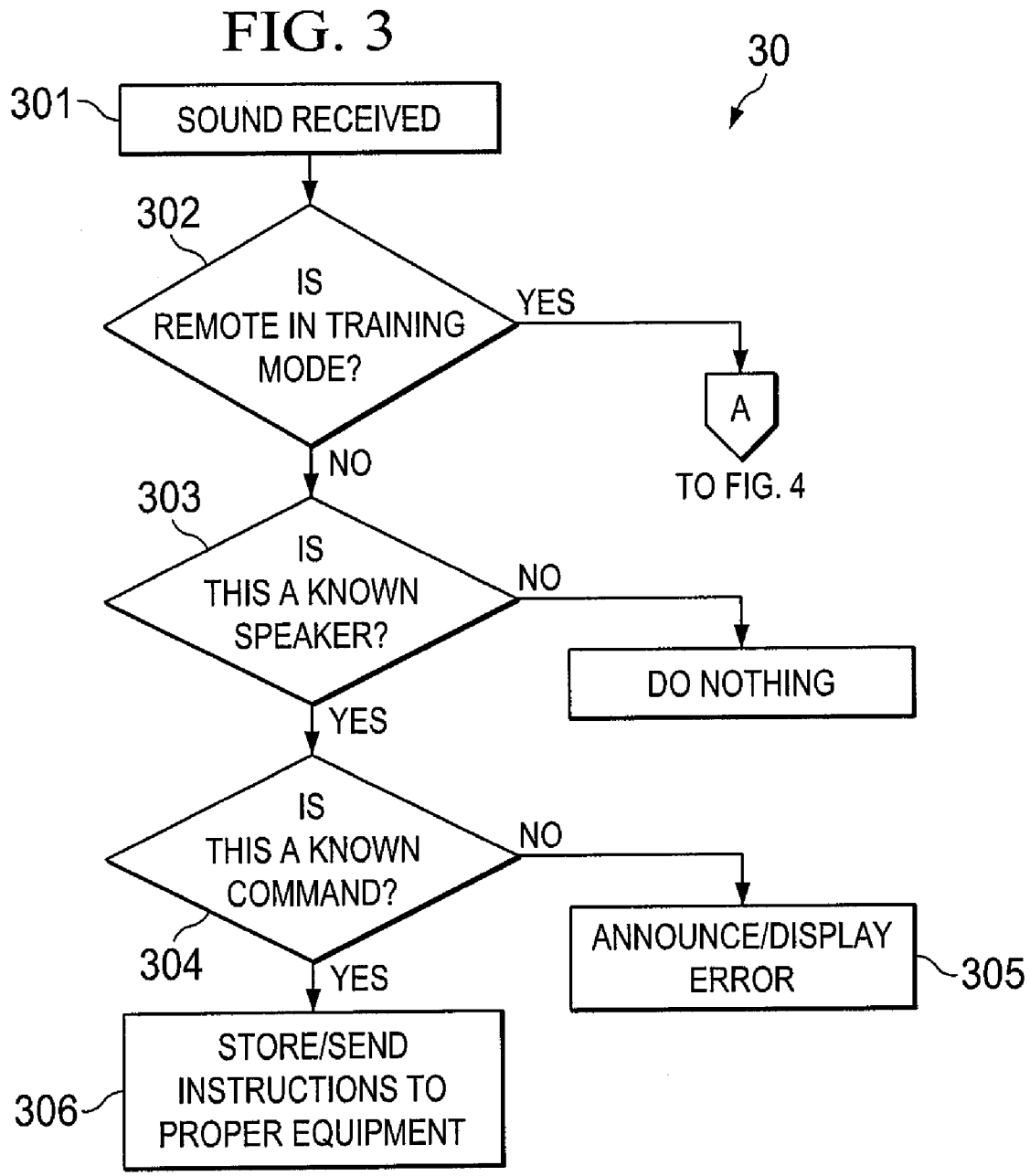

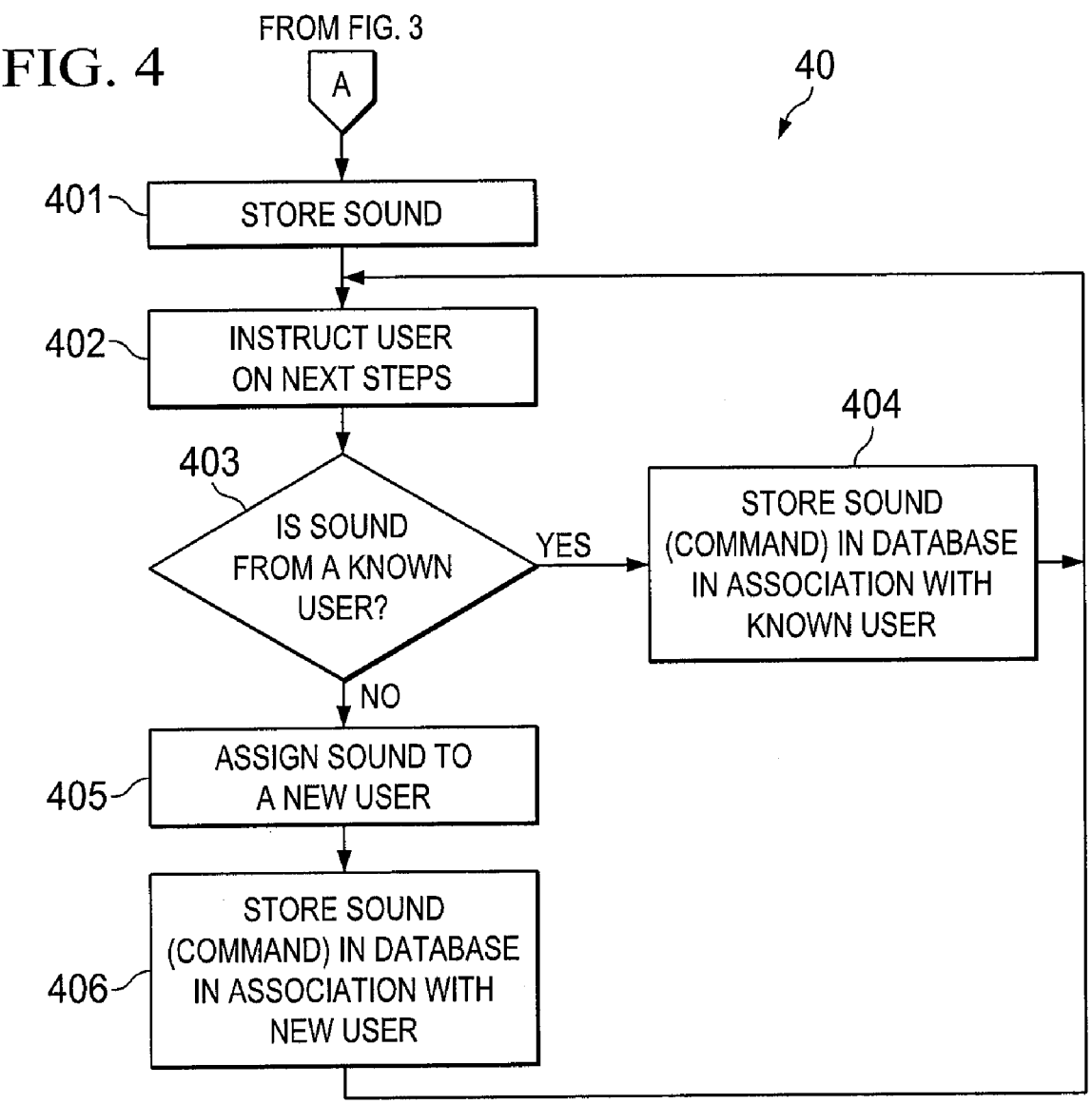

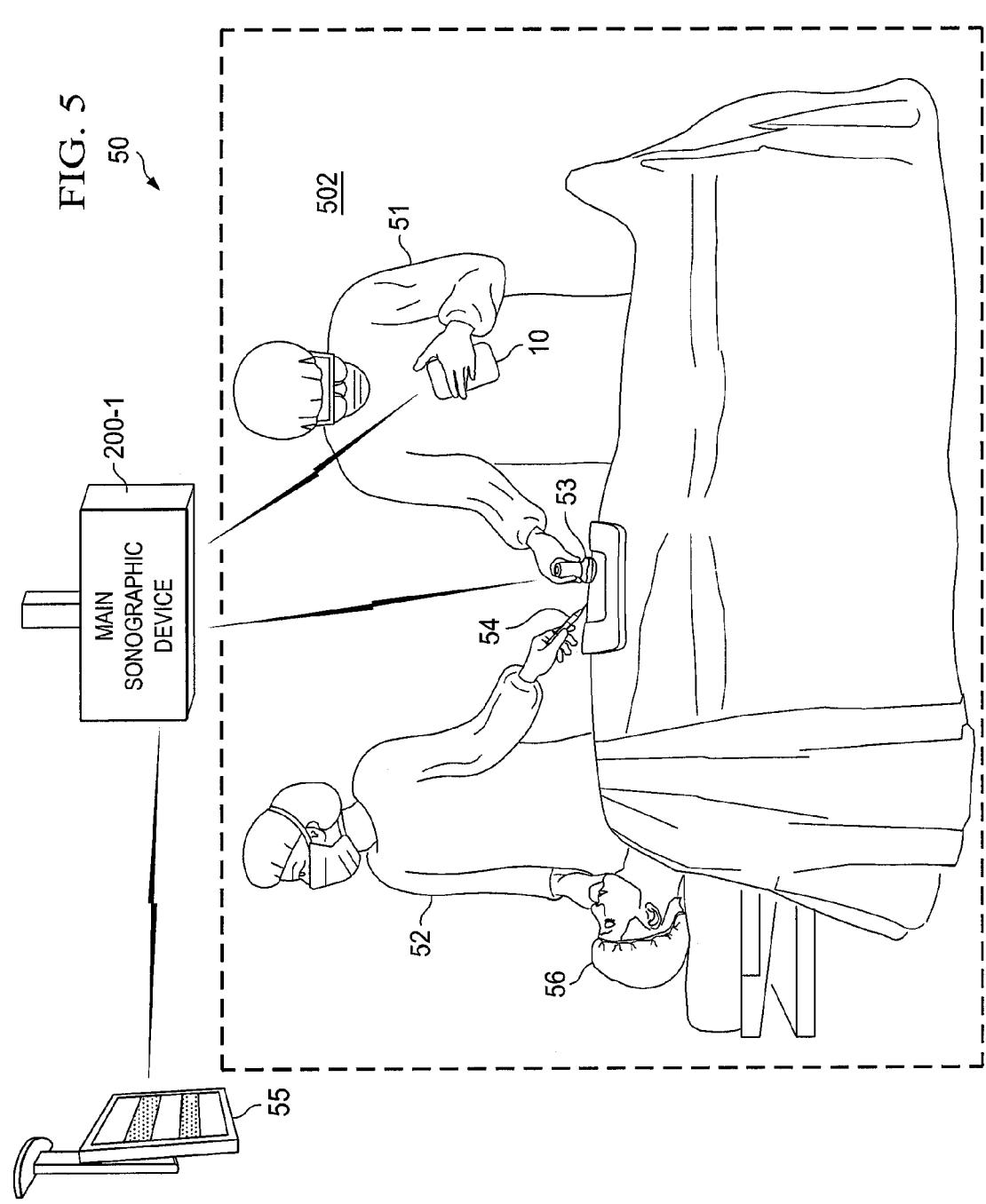

REMOTE CONTROL DEVICE

BACKGROUND OF THE INVENTION

There are many situations were medical equipment, such as sonogram devices, must be used in a sterile environment. When such equipment is used in a sterile environment the person using the equipment (a sonographer in the case of sonographic devices) must from time to time interact with the device controls for a variety of reasons. However, because of the sterile conditions the sonographer must have a method of interaction with the equipment that will not compromise the sterile environment.

Some areas of particular concern occurs when sonography is used for assisting with nerve blocks and peripherally inserted central catheter (PICC) lines both of which procedures must be performed in sterile environments. Thus, the patient is sterile, the doctor and nurses are sterile, but the sonograph machine is sitting a way from the sterile zone and is not sterile. If the operator were to touch the machine, as would occur in order to manually adjust a dial or operate a switch, the operator would no longer be sterile. Since various machine operations, such as depth and gain adjustments, must occur during the procedure the operator must interact with the sonogram machine several times during the course of a procedure.

One method for dealing with this issue is to use a second person who physically interacts with the machine outside of the sterile zone based upon instructions given by a person within the sterile zone. Using two people is costly and inefficient.

One method of eliminating the second person is for the person in the sterile environment to use a fresh sterile gauze pad (usually a 4×4 pad) every time the sonogram machine is to be touched. This presupposes that a stack of such sterile pads are available (which requires planning and prior execution) and also presupposes that the operator can reach the machine, which sometimes is positioned across the patient and sometimes several yards from the patient.

BRIEF SUMMARY OF THE INVENTION

The present invention is directed to a system and method which allows a device user who is within a sterile environment to interact remotely with a device physically located outside of the sterile zone. In one embodiment, the remote link is wireless and allows the operator to adjust critical controls without breaking the sterile environment. The remote device is designed to be sheathed in sterile sheaths and further designed, in one embodiment, to keep the remote control element from physically interacting with the patient and in some cases with the device operator. In one embodiment, the remote device operator interacts with the remote device verbally.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 3 is a flow chart illustrating one embodiment of a method of operation of the remote system;

FIG. 4 illustrates one method for training a remote unit to be user specific; and FIG. 5 shows an operating theater having both sterile and non-sterile environments.

DETAILED DESCRIPTION OF THE INVENTION

Figure 1:
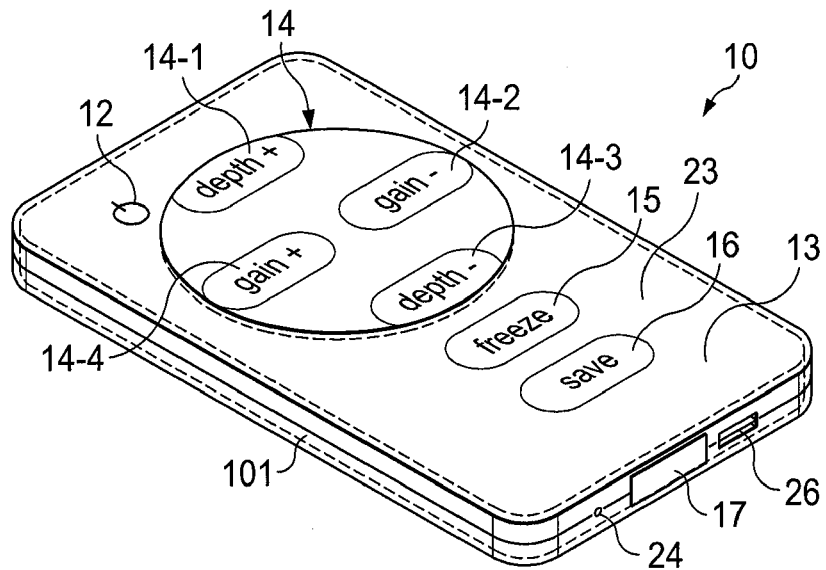
FIG. 1 illustrates one embodiment of a remote control device in accordance with an aspect of the invention.

FIG. 1 illustrates one embodiment of a remote control device, such as device 10, in accordance with an aspect of the invention. Device 10 contains shell 101 and key pad 23. The key pad wraps around the internal circuit board (not shown) and seals against the shell. The key pad acts as a seal to the unit and also encloses the battery case. This provides a very clean back and side surface without screw holes to trap grunge and germs. The battery, in this embodiment, is charged inductively.

In one embodiment, key pad 23 is a single piece of silicon ballistae having an anti-microbial surface that is easily cleanable. Key pad 23 stretches over the entire top surface of the remote device making it easier to clean. In one embodiment, the silicon is stretched over two-part shell 101 and tucked in between the two parts of the shell prior to the top half of the shell being bonded to the bottom half.

Dimensions of device are, in one embodiment, about 2½ inches by 4 inches by 0.75 inches deep. The example shown in FIG. 1 has six buttons plus power button 12. Power button 12 can, if desired, be touched located on shell portion 101 and an on-off light be made visible through pad 23. Four buttons, are arranged around circular bezel 14. These buttons are depth up 14-1, depth down 14-3, gain plus 14-4 and gain minus 14-2. Two additional buttons 15 and 16 control freeze and save, respectively. If desired, any button could be reprogrammed to do other things. There are LED indicators (not visible) to indicate when the device is charging, when it is in training mode, when it is in use, and when it is connected to the main sonographic equipment, etc.

The buttons are positioned and/or sized so that they can be used by feel even without reading the button labels and even without seeing the buttons. In one embodiment, the buttons are not of uniform size or positioned with uniform spacing allowing a user to navigate based on size and relative position of the buttons. The control buttons are thus arranged in an asymmetrical manner, so the user can feel when he/she is at the top of the device versus the bottom of the device. There's also a physical marker on the back to indicate device orientation. In some embodiments, small bumps are positioned on the keys to indicate when a finger is over the top of a particular button.

Note that the keys do not come through openings in the surface but rather are part of the surface structure. The elimination of openings in the keypad surface eliminates potential for liquid and other unwanted material from entering the device and also eliminates areas where germs and bacteria can accumulate. In this manner, the remote input device can receive an input stimulus from a user without physically penetrating a surface of the input device. The remote input device can then process the received stimuli and send one or more command messages to at least one medical device physically located away from the remote input device. Thus, the input device can control at least a portion of a medical procedure being performed on a patient in close proximity to the remote input device. The medical device can then send adjusted parameters, such as power levels, beam forming, etc. with respect to a medical procedure being performed on the patient.

The keys can be programmable so that from time to time the function of a key could change, or the function of the key can be made to change in context to a stage of a program that is currently being controlled. In addition, the device can be set up, for example, with microphone 24 so that the user can issue verbal commands thereby avoiding, or at least minimizing, the need to physically contact the remote device. Voice activation can be specific to a particular user such that commands in the room from other than a "taught" user have no effect.

In some embodiments, the remote device can be set up to handle different main devices. Thus, it becomes a personal assistant to a particular user (or group of user's) controlling different pieces of sonographic equipment located in the vicinity of the user at any point in time. If desired, a personalized label, such as label 17, can be added so the user whose voice is trained on a specific device can recognize the device.

If desired, the entire remote device can be clipped onto the user and can be fully, or primarily, responsive to voice commands. All of the commands, whether by voice or by touching a control key, would be relayed wirelessly (or by wire, if desired) to main sonographic device, such as to device 200-1, FIG. 2. Note that the commands from remote device 10 could, if desired, be delivered to more than one piece of equipment which need not all be sonographic devices.

In one embodiment, the microphone can be built in (as illustrated) and in other embodiments the microphone can be external (not shown) and can communicate with device 10 wirelessly (for example, using Bluetooth) or by a cord and plugged into device 10.

Figure 2:
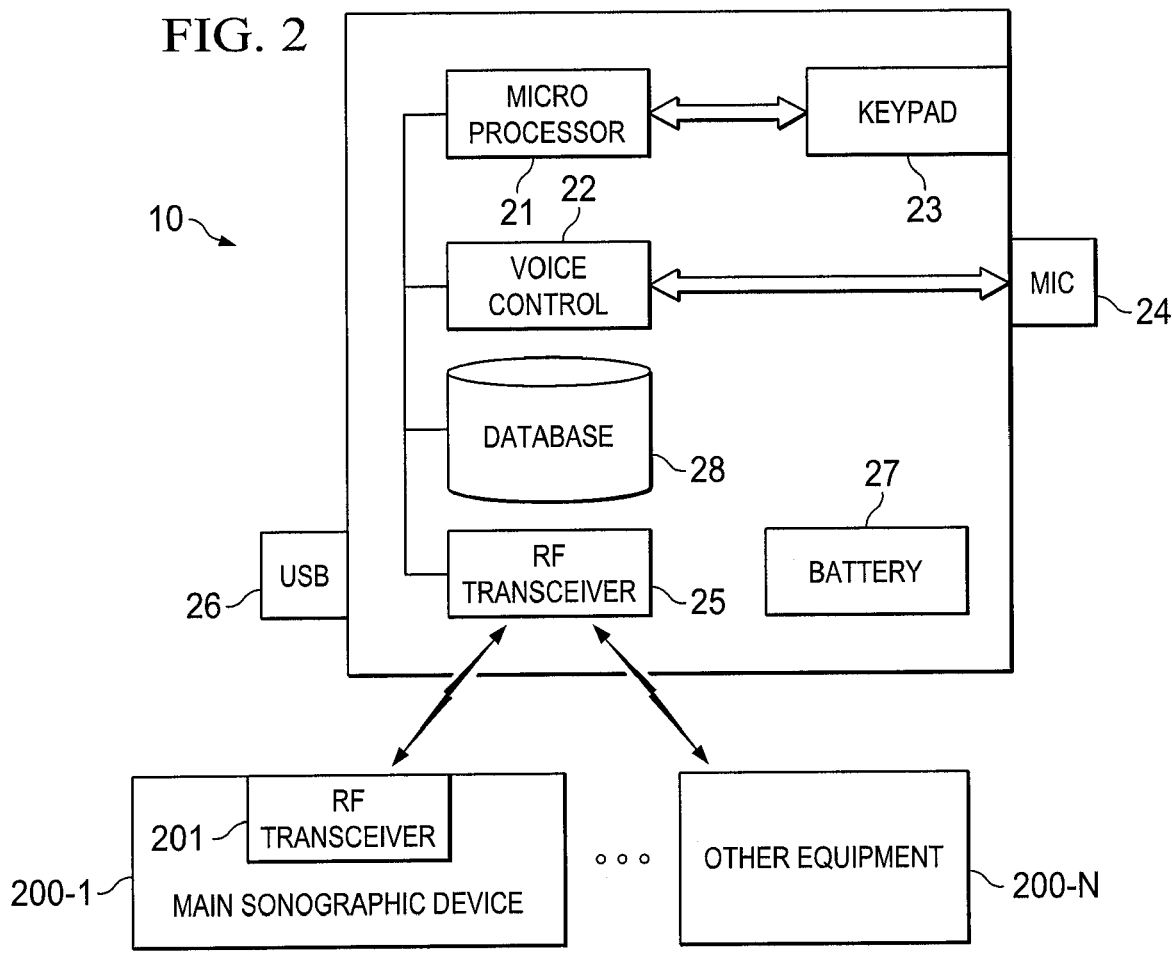
FIG. 2 is a block diagram of one embodiment of the control circuitry for the device shown in FIG. 1.

FIG. 2 is a block diagram of one embodiment of the control circuitry for device 10 shown in FIG. 1. As illustrated, the remote device includes microprocessor 21, voice control unit 22, and RF transceiver 25. The microprocessor controls the remote device and can be set to follow one or more programs stored, for example on code, therein (or in separate memory, not shown). The programs could be changed or updated from time time, for example, via data received though port 26 from an external source such as one of the equipment 200-N.

Processor 21 receives its input command via keypad 23 or via voice control 22 or through USB port 26. Commands can be sent, as will be discussed in more detail with respect to FIGS. 3 and 4, to the microprocessor to program the voice control unit in a training mode. The microprocessor determines whether communication to main sonographic device 200-1 is between RF transceiver 25 and RF transceiver 201 or between port 26 and a port on main sonographic device 200-1 As will be seen, the remote device can control other equipment, such as equipment 200-N. A computer, having a database can be one of the other equipment and can store information from one or more patients or could supply settings or other data to the remote control device. The communication from the other equipment can be routed through a sonographic device, such as through device 200-1 or directly to device 10.

Voice control 22 has an interface through microphone 24 and has both a learning mode and an operational mode. During learning mode it learns, as is well-known, a user's voice signature. If voice control is not used, the input is through one of the six buttons on the keypad as discussed above. Remote device 10 has at least one battery 27 which can be changed from time to time or preferably charged through a speed connector not shown, or, if desired, via inductive charging.

Voice control 22, for example, could be obtained from Sentry and would actually perform the digital signal processing internally by matching the voice signature that is stored on the voice control unit, or external to the unit, for example, in database 28, with the voice that is coming in from the user. In one embodiment, the remote device could have a handshake routine with the main sonographic device so as to allow for sharing of remote devices among several medical or other devices. Database 28 could also be used to store program code for controlling processor 21, voice control 22 keypad 23 and/or RF transceiver 25. In a preferred embodiment, database 28 is part of processor 21.

When the remote device is being used as a personal assistant, it could, for example, record notes and various other inputs before, during and after the procedure. During the procedure, in addition to storing notes from the user, it would, if desired, be used to control the sonographic device, such as beam forming angles, depth, axis orientation, etc. The notes and other information could be immediately communicated (in real time) to a computer separate from the sonographic device, or the data can be stored local and sent in delayed time after the procedure is completed.

In some situations, the information already on file, for example in some other equipment, such as equipment 200-N, could be uploaded to the remote device in order to set the various fields. One example, would be that the user would say, "patient Jane Doe, 57 year old female, here for a nerve block. She has diabetes and high blood pressure." Based on this input, setting information can be uploaded to the remote device and then sent onto the main device or delivered directly via a wireless or wireline (neither shown) from device 200-N to device 200-1.

In addition, while not shown, the keys could be replaced or supplemented by a screen display that could be used both for input and for presenting to a user, or a physician, selected images as required. Also, the screen could be used for handwritten input.

Since the remote device is an input device to the main sonographic device any number of different input methods can be used. One could envision embedding a bar code reader, or a camera, or a scanner all used to input data into the system to provide records and retention for the procedure being performed.

FIG. 3 is a flow chart illustrating one embodiment 30 of a method of operation of the remote system. Sound is received by process 301 and process 302 determines if the remote device is in the training mode. If it is, the incoming sound is processed as will be discussed with respect to FIG. 4. If the system is not in the training mode then process 303 determines if the sound is coming from a known user (speaker). If it is, then process 304 determines if the sound is a known command. If not, then process 305 communicates to the user that the command was not understood. This communication can be, audible, visual or even motion, as by vibrating the remote.

If the command is understood the proper instruction is sent to the proper equipment for execution by that equipment. Note that the same command word from different speakers could, if desired, result in commands to different external equipment, or in some cases the same command from different speakers could result in different commands going to the same equipment. For example, a sonographer could issue the command, "brighter" and the command sent to the main equipment from the remote (as translated, for example, by processor 21 operating in conjunction with database 28) could be to change the angle of the beam former. However, if the physician (assuming he/she were a trained speaker on the system) were to say, "brighter" the command to the main sonographic equipment might be to brighten the readout display. Alternatively, the remote device could be set up such that when the physician said, "brighter" the intensity of the lighting over the visual operating field of the patient could be increased.

FIG. 4 illustrates one method 40 for training a remote unit to be user specific. If the remote device is in the training mode (either under manual control or by a voice command) when a verbal command is received, process 401 saves the sound to a database and process 402 then instructs the user as to the next steps in the training process. This could be to have the user repeat the command a few times, or to say specific commands, or a combination of instructions.

Process 403 determines if the sound is from a known user and if it is the sound is stored by process 404 in a database in association with a known user. The process then would receive instructions as to what device the instruction pertains and what command should be associated with the instruction. Thus, in the example above, the command "brighter" from user A (sonographer) would be saved in association with a command to change beam forming angles on machine 200-1 while the command, "brighter" from user B (physician) would be in association with a command to the lighting system to increase intensity.

If the incoming sound were not recognized as belonging to a known user then process 405 would assign a new user id to the sound and process 406 would store the sound in the database in association with the new user. Then subsequent sounds arriving would be processed by processes 403 and 404 as above-described for known users.

FIG. 5 shows operating theater 50 having both sterile and non-sterile environments. Main sonographic equipment 200-1 is located outside of sterile environment 502 and could be in the same room or even in a different room from patient 56. As illustrated, sonographer 51 controls probe 53 which is in communication, either wirelessly or via wireline, with device 200-1, and, if desired, with device 10. Probe 53, in this embodiment, is used to send sound signals into the patent and to receive reflected signals back from the patient for processing by device 200-1. Images 54 are formed from the processed signals are displayed on display 55, which in this example would show catheter 54 being inserted into and artery by physician 52. If desired, the image could also be displayed on device 10.

The sonographer has remote device 10 which is used to control device 200-1. As discussed, when the remote device responds to verbal commands it can be pinned to the sonographer, or hang around his/her neck. In some situations, the remote device can be in a pocket with the microphone separate therefrom. Communication from the microphone, which could be held under a sterile mask covering the sonographer's mouth to the remote device can be, for example, by Bluetooth transmission.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system for controlling medical devices, said system comprising:
   a remote device adapted for to be located within a sterile environment and operable by a user also within said sterile environment for interfacing with a medical equipment outside of said sterile environment, said remote device being sealed to avoid contamination while still receiving input stimuli from said user, wherein said remote device includes control buttons arranged in an asymmetrical manner and integrated into a surface of said remote device such that said buttons do not create openings in said surface; and
   wherein said remote device contains at least one communication interface for linking said remote device to at least one said medical equipment, said interface operable for transporting electrical signals from said remote device to said medical equipment for at least partially controlling said medical equipment.

2. The system of claim 1 wherein said remote device comprises:
   a sealed surface having constructed therein at least one area for allowing interaction with said user.

3. The system of claim 2 wherein said sealed surface comprises single piece of silicon ballistae having an anti-microbial surface, said silicon having formed therein areas for facilitating said user interactions.

4. The system of claim 3 wherein said formed areas are human touch sensitive.

5. The system of claim 1 wherein said medical equipment controls at least one probe within said sterile environment, said probe being separate from said remote device.

6. The system of claim 5 wherein said medical equipment is sonographic equipment.

7. The system of claim 6 wherein said electrical signals are bidirectional.

8. The system of claim 1 wherein said stimuli is at least one verbal command from said user.

9. The system of claim 8 wherein said remote device is trained to understand verbal commands unique to said user.

10. The system of claim 1 wherein said remote device further comprises:
    means for communicating with multiple equipments outside of said sterile environment, one said equipment operable for uploading data to said medical equipment through said remote device, said uploaded data pertaining to desired settings of said medical equipment.

11. The system of claim 10 wherein said desired medical settings correspond to a specific patient within said sterilized environment, said patient identified via said remote device.

12. The system of claim 1 wherein said remote device comprises: voice control for recognizing specific commands from specific users.

13. The system of claim 12 wherein said remote device further comprises: a processor for directing a command communication to a specific piece of equipment outside said sterile environment in response to recognized ones of said commands.

14. A method for controlling medical devices, said method comprising:
sending command messages from a remote input device to at least one medical device physically located away from said remote input device, said remote device having one or more control buttons that are not spaced uniformly throughout said remote device and are integrated into a surface of said remote device such that said buttons do not create openings in the surface, wherein at least one of said medical devices is a sonographic device, said medical device controlling at least a portion of a medical procedure being performed on a patient in close proximity to said remote input device; and
receiving back from said medical device adjusted parameters with respect to said medical procedure being performed on said patient, said parameters controlling, at least one ultrasonic parameter of said sonographic device.

15. The method of claim 14 further comprising:
receiving an input stimulus from a user at said remote input, said stimulus received without physically penetrating a surface of said input device, and wherein said command message is controlled by received ones of said input stimuli.

16. The method of claim 15 wherein said input stimulus is received through a single piece of silicon ballistae.

17. The method of claim 16 wherein said silicon has an anti-microbial surface.

18. The method of claim 15 wherein said input stimulus is a voice command.

19. The method of claim 18 wherein said voice command is taught with respect to a specific user.

20. The method of claim 18 wherein said voice commands are specific to multiple users.

21. The method of claim 14 wherein said sonographic device having a probe in proximity to said input device, said parameters controlling, at least in part, said probe.

22. A remote input device comprising:
a processor;
a transmitter;
a sealed interior area surrounding said processor and said transmitter;
one or more control keys that are not of uniform size relative to the other control keys and incorporated into a surface of said remote device such that said keys do not create openings in said surface;
said processor operable for accepting input stimuli from external to said interior area, said stimuli accepted without compromising said sealed interior; and
said transmitter operable under control of said processor for sending commands to a sonographic equipment at a location physically separated from a location of said remote device, said commands controlling at least one ultrasonic parameter of said sonographic equipment.

23. The input device of claim 22 wherein said sealed interior is formed by a surface area having constructed therein at least one area for receiving said stimuli.

24. The input device of claim 23 wherein said surface area comprises: a silicon ballistae having an anti-microbial surface.

25. The input device of claim 22 further comprising: voice control for accepting input stimuli in the form of voice commands.

26. The input device of claim 25 wherein said voice control is trainable with respect to commands and users.

27. The method of claim 14 wherein said ultrasonic parameter comprises one or more of a power level, beam forming angle, depth, or axis orientation.

28. The input device of claim 22 wherein said ultrasonic parameter comprises one or more of a power level, beam forming angle, depth, or axis orientation.

* * * * *